United States Patent [19]

Loesche

[11] Patent Number: 4,568,535

[45] Date of Patent: Feb. 4, 1986

[54] COMPOSITION FOR PERIODONTAL ADMINISTRATION

[76] Inventor: Walter J. Loesche, 1814 Hermitage, Ann Arbor, Mich. 48104

[21] Appl. No.: 631,542

[22] Filed: Jul. 16, 1984

Related U.S. Application Data

[63] Continuation-in-part of Ser. No. 405,790, Aug. 6, 1982, abandoned.

[51] Int. Cl.$^4$ .......................... A61K 9/22; A61K 9/52
[52] U.S. Cl. .................................... 424/19; 514/365; 424/28
[58] Field of Search .................. 424/22, 26, 28, 19, 424/273 R, 52; 106/35; 514/365

[56] References Cited

PUBLICATIONS

Soskolne et al., New Sustained Release Dosage Form of Chlorhexidine for Dental Use, J. Perio, Res, 18:330–336.

*Primary Examiner*—Johnnie R. Brown
*Assistant Examiner*—C. Joseph Faraci

[57] ABSTRACT

A composition for periodontal administration and a method of periodontal treatment involving a slow release device which can be placed directly into the periodontal pocket where metronidazole, with or without antioxidants, are released over periods of days to weeks at a cidal concentration for anaerobes in the domain of the periodontal pocket.

2 Claims, 3 Drawing Figures

PROFILE OF THREE TEETH SHOWING TWO CONTOURED DRUG RELEASING FILMS 36 SUBGINGIVALLY PLACED ONLY IN THOSE SITES WHERE THE POCKET DEPTHS ARE 6 MM OR MORE. NOTE THAT THE FILMS CAN BE PLACED OVER THE BIFURCATION SITES 25.

COMPOSITION FOR PERIODONTAL ADMINISTRATION

CROSS-REFERENCES

This is a continuation-in-part of Ser. No. 405,790 filed 8/6/82 now abandoned.

BACKGROUND OF THE INVENTION

1. Technical Field

This invention relates to a composition for periodontal administration that is cidal for anaerobes in the domain of the periodontal pocket and to a novel method of treatment of anaerobic infections in periodontal disease that is dependent upon the slow release of metronidazole from a plastic film that is placed within the periodontal pocket, and which film resides in such pocket for a period of days to weeks.

2. Description of Prior Art

The main cause of tooth loss in adults is periodontal disease. Yet, surprisingly, less than one percent of the public expenditures for dental treatment is for periodontal disease (see J. Dent. Educ. 43:320, (1979). This is because conventional periodontal treatment is too expensive for most individuals, mainly due to the labor intensive, symptomatic treatment that is usually performed by highly skilled specialists.

Periodontal disease is an all-inclusive term for a variety of clinical entities that are forms of either gingivitis or periodontitis. Gingivitis is an inflammation of the gingiva or gums that can be associated with poor oral hygiene and/or hormonal states of the host. It is assumed, but not proven in the human, that gingivitis will progress to a periodontitis, which is the form of the disease in which the infection has progressed to involve the oral tissues which retain the teeth in the jaw bone. Periodontitis is the more severe form of the disease, and if untreated, will eventuate in the loss of the tooth.

Dentists have long assumed that periodontal disease originates by the overgrowth of bacteria on the tooth surfaces in aggregates known as dental plaque. If this plaque persists for long periods of time on the tooth surfaces, it may in some instances calcify, forming the hard substance known as calculus. Numerous studies describe chemical agents which can in vitro and in vivo reduce plaque formation and calculus. However, none of these chemical agents has been reported to be successful in treating periodontitis.

A substantial number of different types of compounds and compositions have been developed for use as antibacterial and antiplaque agents, e.g., benzethonium chloride and cetyl pyridinium chloride, disclosed in U.S. Pat. No. 4,110,429, or as anticalculus agents, e.g., 2-phosphono-butane 1,2,4-tricarboxylic acid, disclosed in U.S. Pat. No. 4,224,308. These compounds are designed to be used by the individual in dentifrices, dental powders, pastes, mouthwashes, nonabrasive gels, chewing gums, topical solutions and the like, e.g., see U.S. Pat. No. 4,205,061. They are designed to be used as prophylactic agents, usually without requiring a prescription or supervision during usage, e.g., see U.S. Pat. No. 4,251,507. Often they are compounded with detergents and other cleaning agents, and this cleaning action is often an important aspect of the invention, e.g., see U.S. Pat. Nos. 4,251,507 and 4,205,061. None of these compounds or compositions are designed to be used as antimicrobial agents for the treatment of periodontitis, nor are they formulated to be slow release devices for these antimicrobial agents in vivo.

Recent research in periodontal disease (see, for example, Chemotherapy of Dental Plaque Infections, Oral Sci. Rev. 9:65–107, 1976) indicates that gingivitis and periodontitis are characterized by different types of bacteria. Gingivitis is associated with the accumulation of gram positive cocci and actinomyces, whereas periodontitis is characterized by proportional increases in anaerobic bacteria, such as spirochetes and black pigmented bacteroides (see Host-Parasite Interactions in Periodontal Disease. R. J. Genco and S. E. Mergenhagen, eds. Amer. Soc. for Microbiol. Washington, D.C. p. 27–45, 62–75, 1982). The different bacterial compositions of plaque associated with either gingivitis or periodontitis suggest that a mode of treatment that is effective in gingivitis may not be effective in periodontitis. This is an important factor in the present invention, as previous discoveries in the area of periodontal disease have assumed that there is no bacterial specificity in periodontal disease. This is now known to be incorrect. These bacterial differences in plaque may explain why an agent effective in plaque control, such as chlorhexidine, has little effect on gingivitis and no published effect on periodontitis.

Another important finding from recent periodontal research is that the composition of the dental plaque will differ according to its location on the tooth surface. Above the gingival or gum margin, facultative bacteria, such as gram positive cocci and rods, are numerically dominant, whereas below the gum margin, anaerobic motile bacteria such as spirochetes, and anaerobic gram negative rods including the black-pigmented bacteroides are predominant. In other words, two different microbial ecosystems are present on the same tooth surface.

This is illustrated in the accompanying drawings in FIGS. 1a and 1b, which show a cross section of a tooth 10, a periodontal pocket 11, and the gingiva or gum 12. The tooth illustrated in FIG. 1a exhibits periodontal disease in which periodontal attachment of the tooth to the alveolar bone has been destroyed, and a periodontal pocket 11 has been formed between the gum 12 and the root surface of the tooth. Clinical assessment of such deterioration of teeth is made by measuring the depth of the pocket. This is done by inserting a periodontal probe or ruler, a thin metal rod (not shown), to the base of the pocket 14. Two measurements can be obtained with the probe. One, called the pocket depth x, in illustration 1a is the distance between the height of the gingival margin 13 to the base of the pocket 14. The other measurement, y, is the distance between the height of the gingival margin 13 and the cementoenamel junction (CEJ)15. The CEJ is extremely valuable because it gives a permanent reference mark on each tooth surface from which one can base further measurements. It enables one to divide the pocket depth measurement into two components: the distance between the CEJ and the top of the gingival margin, y, and the distance between the CEJ and the bottom of the pocket, z. This letter measurement is called the attachment distance. As illustrated in the diseased tooth, the attachment distance is 5 mm and the pocket depth is 8 mm.

FIG. 1b is an enlargement of a section of the type shown in FIG. 1a in which the periodontal pocket 11 is now filled with bacterial plaque. Note that the plaque lies between the tooth and the gingiva in the space called the periodontal pocket. Also note that the bacterial composition of the plaque varies according to its spatial relationship to the gingival margin 13. Above the gingival margin the plaque is known as the supragingival plaque, and it generally has equal numbers of gram positive (+) cocci and rods, fewer gram negative (−) rods and even fewer motile rods. Next comes a section of plaque which contains proportionally more gram negative (−) rods and some spirochetes. This plaque is known as the gingival margin plaque. Finally, in the bottom of the pocket, is found a plaque which is dominated by anaerobic gram negative rods and motile rods, including black-pigmented bacteroides and spirochetes. This plaque is known as subgingival or pocket plaque and it is this plaque that is the etiologic agent of periodontitis.

It is clear from this illustration and from recent electronmicroscopic examinations of plaque that the subgingival plaque is distinct from supragingival plaque (see J. Periodontol. 47:1-18, 1976). This has important implications for our invention, as previous patents for the use of antimicrobials described agents that are delivered to the supragingival plaque. It can be surmised from the illustration and now accepted as fact, that antimicrobial agents delivered in dentifrices, dental powders, pastes, mouthrinses, nonabrasive gels, chewing gums, topical solutions and the like, will minimally penetrate into the pocket for a distance of about 1 to 3 mm. As periodontal pockets may be 12 to 13 mm in depth, it is apparent that the topical application of any antimicrobial agent, even metronidazole, to the supragingival plaque will have no or minimal effect on the subgingival plaque and accordingly, should have little if any effect on periodontitis. Our invention is, therefore, quite distinct from the topical application of metronidazole in water or in vehicles, such as gels or pastes as disclosed in U.S. Pat. No. 3700,685, as our invention will place the metronidazole directly into the periodontal pocket, where it will be in contact with the bacteria in the subgingival plaque. Also, our invention is different from previous patent applications which incorporated antimicrobials in dentifrices, gels, powders, etc. which were designed to be delivered to the supragingival tooth sites, e.g., see U.S. Pat. Nos. 4,205,061, 4,251,507, 4,224,308 and 3,700,685 and had as their treatment goal, the control of dental plaque and oral cleanliness.

From a review of these patents and other information in the literature it is apparent that an improved means of treating periodontitis is needed in dentistry. From a reading of information in the art, it is obvious that the basic need of treating an anaerobic infection in the periodontal pocket is not satisfied. None of the means presently available appears to get at the heart of the problem, which is finding an improved means of delivering an antimicrobial agent specific for anaerobic organisms, such as spirochetes and black pigmented bacteroides, to the periodontal pocket for continuous periods of 5 to 10 days or more.

Such a delivery can be achieved with systemic antimicrobials. Indeed, short-term oral administration of metronidazole in humans and in dogs caused a sustained reduction of spirochetes and black pigmented bacteroides for weeks to months (see for example J. Clinical Periodontol. 8:29-44, 1981, ibid 10:100-112 1983). However, as is known, such systemic usage of metronidazole can be associated with undesirable side effects, such as nausea. Also, there is the suggestion from animal toxicity studies that metronidazole is a weak tumorigen (for example, see Proceedings of International Metronidazole Conference, Excerpta Medica, 1976). For these reasons, it is desirable to use the lowest possible dosage of metronidazole consistent with a therapeutic effect. The slow-release-film-metronidazole device, which is described in this invention, may reduce the amount of metronidazole necessary to treat advanced cases of periodontitis by as much as 99%.

Thus, the present invention not only describes an effective means of treating anaerobic periodontal infection, but does so at dosages that are greatly reduced compared to systemic or oral administration of the same agent(s). This safety factor is an important aspect of the present invention.

DETAILED DESCRIPTION OF THE INVENTION

Figure 1:
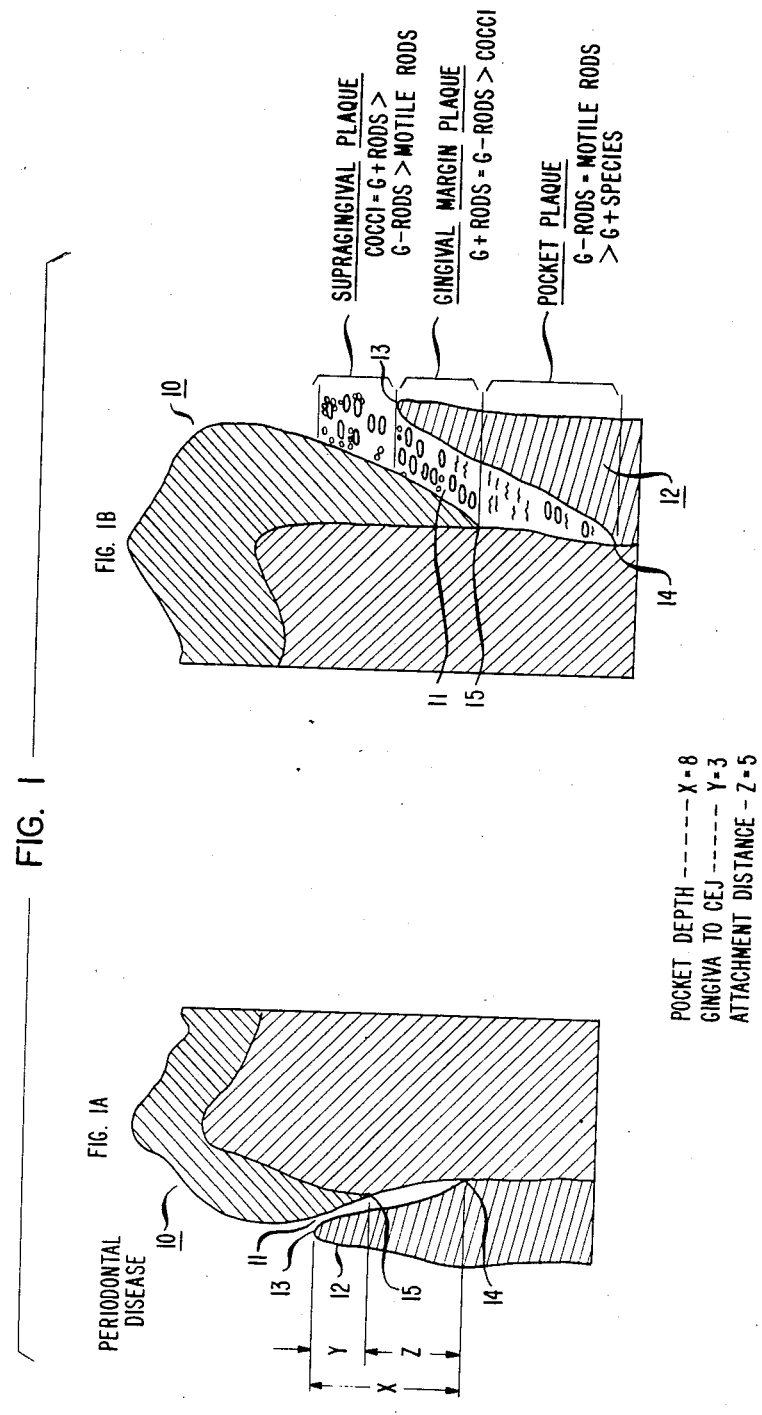

It is an object of the present invention to provide improved means for treating periodontal infections, such as periodontitis which occur below the gingival margin in the periodontal pocket.

It is another object of the invention to provide means of distributing metronidazole, or other antimicrobial agents, to the peridontal pocket that avoids the disadvantages of the prior art.

It is another object of the invention to incorporate metronidazole, or other antimicrobial agents, in a slow release device that can be placed by the clinician directly into the infected periodontal pocket.

It is a further object of the invention that the slow release device will release metronidazole, or other antimicrobial agents, over a period of 5 to 10 days or more.

It is a further object of this invention that the release of metronidazole, or other antimicrobial agents, by the slow release device will significantly reduce and/or eliminate the levels of periodontopathic bacteria residing in the periodontal pocket.

Other objects of this invention will be set forth in, or be apparent from, the following description of the invention.

A novel means for accomplishing the foregoing objects and other features and advantages of the present invention are achieved by incorporating metronidazole (Zenith Laboratory, Northvale, N.J.), or other antimicrobial agents, in a polymer, such as ethylcellulose (Hercules, Inc., Wilmington, Del.), which can be placed directly into the diseased periodontal pocket by the clinician. Such metronidazole-ethylcellulose films will release metronidazole continuously into the pocket over a period of 7 to 14 days or more.

The present invention concerns a composition for subgingival administration of an antimicrobial agent directly to the periodontal pocket in patients exhibiting periodontitis. The composition comprises a pharmaceutically acceptable polymeric matrix, such as ethylcellulose, (see J. Dent. Res. 54:1392, 1980), which contains metronidazole. The polymer-metronidazole combination is formulated so that the metronidazole is slowly released from the polymer into the environment of the periodontal pocket. For purposes of this invention one uses a concentration of metronidazole such that a single dose of the composition provides sustained release of metronidazole for 7 to 14 days or more. A preferred dosage for a periodontal pocket, for example, is one in which each pocket receives about two mg of metronidazole, preferably in a slow release form that releases from 0.01 to 0.2 mg per day for each day that the polymeric device remains in the periodontal pocket.

A preferred anti-periodontitis formulation is given hereinafter by way of example and is presented for the purpose of illustration but not of limitation.

In this regard, the invention contemplates a preferred embodiment in which metronidazole comprises 1 to 20% wt/wt of the ethylcellulose film. Such a film is achieved by slowly dissolving 20 g of metronidazole (Zenith Laboratory) in chloroform, followed by 80 g of ethylcellulose Type N-22 (Hercules, Inc.), so as to form a slurry. Ethylcellulose Type N-7 or N-7NF may also be used. This slurry is then poured or cast into molds, which determine the thickness of the film. The chloroform is allowed to evaporate, leaving behind a thin film in which the metronidazole is enmeshed within the matrix of the ethylcellulose. This metronidazole-ethylcellulose film acts as a slow release device for metronidazole, as is described in the following test procedure.

A circular disc of the film, measuring 5 mm in diameter and 0.3 mm thick was placed on a bacteriological agar medium in a Petri plate that had been previously inoculated with *Bacteroides gingivalis*, a bacterium commonly found in the subgingival plaque and a suspected periodontal pathogen. This bacterium or germ subsequently grew on this medium, except in the vicinity of the disc. In the vicinity of the disc there was a zone of no growth that measured from 1 to 1.5 cm in diameter. This zone of inhibition would have been larger, except that the disc was removed after one day and placed on a second agar plate that also had been previously inoculated with *B. gingivalis*. After a zone of bacterial inhibition was noted about the site where the disc had been placed. This disc was subsequently transferred sequentially to other agar plates, inoculated with *B. gingivalis* and each time a zone of inhibition was noted. The supply of metronidazole in the disc was eventually exhausted after 70 days incubation on agar medium, during which time it was transferred about 55 times. If the disc was made thicker, i.e., about 0.5 mm thick, it could be incubated about 110 days before its supply of metronidazole was exhausted. During this period the disc was transferred about 75 times to fresh bacteriological medium newly inoculated with *B. gingivalis*. Thus the length of time that the disc can release the metronidazole is a factor of the film thickness provided that the composition remains unchanged. In other trials the discs were able to similarly inhibit *Bacteroides intermedius* and the anaerobic spirochete known as *Treponema denticola*. These three species of bacteria are representative of the anaerobic black pigmented bacteroides species and spirochetes respectively that are associated with periodontitis. The fact that these bacteria were inhibited by the disc containing 20% metronidazole, 80% ethylcellulose after 70 to 110 days of incubation during which 55 to 75 serial transfers of the disc occurred, attests to the fact that the formulation described in this invention acts as a slow release device for the metronidazole.

As it is well known in the periodontal literature, the absence of black pigmented bacteroides and spirochetes is associated with periodontal health, and the proportional increase of these organisms is associated with periodontal disease (see J. Clin. Periodontol. 5:115–132, 1978; Host-Parasite Interactions in Periodontal Disease. R. J. Genco and S. E. Mergenhagen, eds. Amer. Soc. for Microbiol. Washington, D.C. pp. 27–45, 62–75, 1982). Thus, antimicrobial agents, which suppress these microbes, have therapeutic value in the treatment of periodontitis. Indeed, in studies in which systemic metronidazole was given for one week and compared to placebo medication, the metronidazole treatment was associated with a significant improvement in periodontal health, as evident by pocket reduction and decreased proportions of spirochetes and black pigmented bacteroides, (J. Clin. Periodontol. 8:29–44, 1980; J. Periodontol. 55:325, 1984).

The usage of a metronidazole-ethylcellulose film, as embodied in this invention, will achieve the same therapeutic result, but at much lower dosages. For example, a standard art-recognized systemic treatment for periodontitis by the oral route using oral tablets requires a total of about 5250 to 7000 mg of metronidazole. However, non-systemic treatment for periodontitis with the slow release composition of the present invention uses only about 2.4 mg per periodontal pocket. As patients with the most advanced cases of periodontitis may have about 20 diseased pockets, and if the metronidazole discs are placed in each of these pockets, then the total dosage of metronidazole would be about 50 mg. This total dosage is less than 1% of the total systemic (oral) dose and reflects a substantial safety factor over systemic treatment with oral metronidazole. Thus, another aspect of the present invention is its outstanding safety factor relative to systemic administration.

Figure 2:
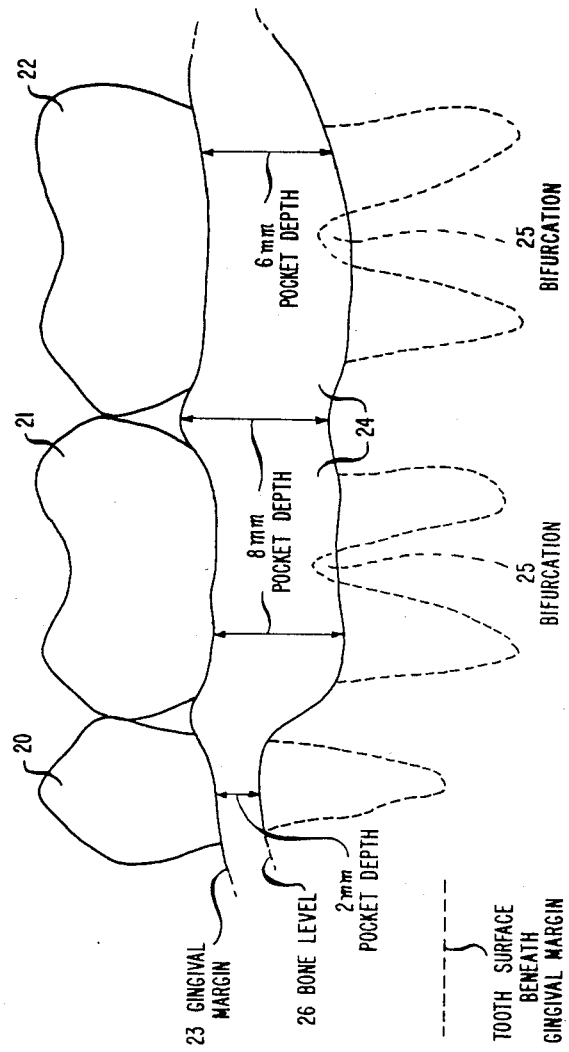
Figure 3:
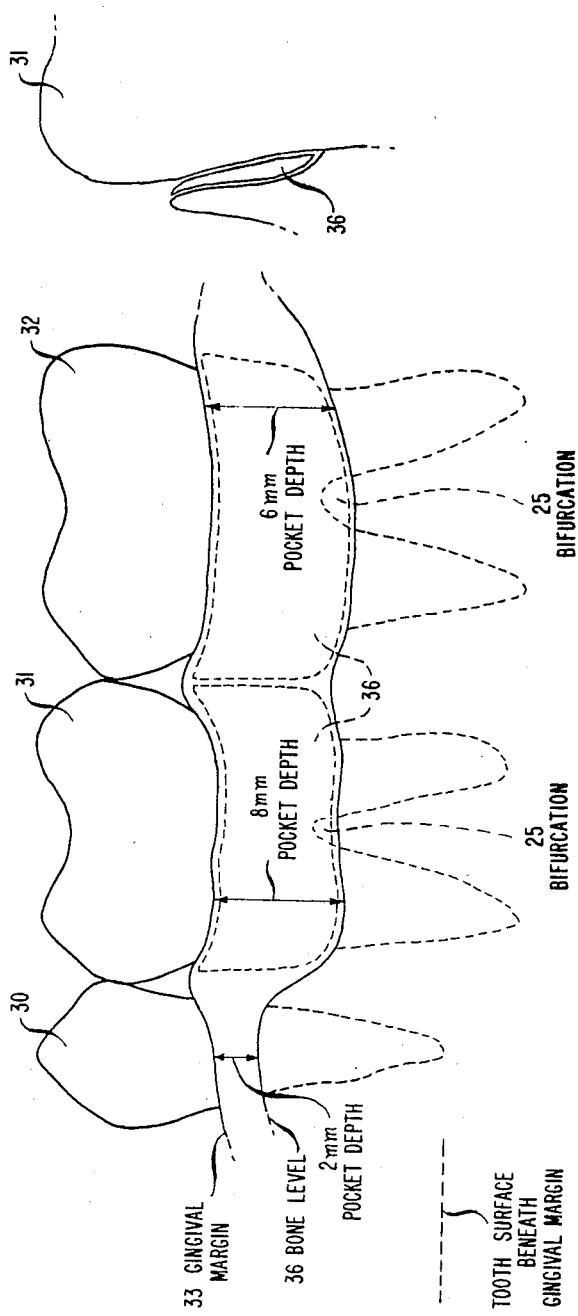

This is possible because the nature of the invention allows the metronidazole to be placed exactly in and to the depths of the pockets where the periodontitis exists. The clinician diagnoses the site where the periodontitis exists and then cuts or contours the metronidazole-ethylcellulose film for each of the individual pockets, so that its resulting contour matches the dimensions and contour of each pocket in turn so that the resulting contoured film can be placed completely and matchingly within all of the pockets below the gingival margin. This is illustrated in FIG. 2, which shows a premolar 20, a first molar 21 and a second molar 22. The gingival margin 23 is that level of gum which is seen about the teeth. The pocket is that space below the gingival margin where the tooth was formerly attached to its supporting tissue. As shown and as expressed dimensionally the difference between the gingival margin and the base of the pocket, i.e. pocket depth 24, about the first and second molars ranges from 6 to 8 mm, and about the premolar, ranges from about 2 to 4 mm. The metronidazole-ethylcellulose film is contoured by the dentist to fit subgingivally in those sites about the molars that have pockets of 6 or more mm. This is shown in FIG. 3, where two such contoured films 36 have been placed in the pockets about the first and second molars. Note in particular the area on the teeth where the roots separate or bifurcate. These bifurcations 25, are notoriously difficult to treat by conventional mechanical debridement and are completely inaccessible to antimicrobials delivered by mouthrinses, dentifrices, gels, etc. However, the film can be placed over and within the bifurcations, thus delivering the metronidazole to this part of the tooth that usually is refractory to most forms of conventional periodontal therapy. Thus, another aspect of the present invention is that bifurcations and trifurcations (root separation on the maxillary or upper teeth) can be exposed to therapeutic levels of metronidazole for periods of time sufficient to treat an anaerobic infection.

The placement of the films in this fashion below the gum line is novel to this invention and has not been described in previous patents devoted to antimicrobials in plaque control, e.g., see U.S. Pat. Nos. 3,700,685, 4,205,061, 4,224,308 and 4,251,507.

Metronidazole's action can be counteracted by the presence of oxygen. As bleeding is a common finding in periodontitis and the oxygen contained in blood may reduce the activity of the released metronidazole, a preferred embodiment of the compositions of the invention includes an antioxidant that is compatible with the formulation. For this purpose, one may use one or more of a wide variety of pharmaceutically-acceptable antioxidant agents that provide the desired oxidation reduction potential for optimal bactericidal action of metronidazole. Such antioxidants include agents such as ascorbic acid, sodium thiosulfate, dithiothreitol, cysteine, thioglycollate and glutathione. Anti-oxidants that are recognized as safe for use as food additives, such as ascorbic acid and sodium thiosulfate, are preferred. One uses an amount of anti-oxidant sufficient, when the composition is administered to the subgingival site or pocket site, to enhance or maintain the anaerobic state of the site during the period of treatment. A preferred composition is one in which the concentration of antioxidant is in the range from about 0.1 to about 1% by weight of the composition. This usage of an antioxidant to enhance the action of metronidazole is novel to this invention.

As indicated, the composition of the invention comprises a pharmaceutically acceptable polymer that is solid at body temperatures. The polymer can be selected from naturally occurring and synthetic polymeric materials and manufactured in composition forms as inserts or containers by known methods. Thus, the invention contemplates use of matrices composed of any of a wide variety of art-recognized polymeric materials, such matrices and their method of manufacture being described, for example, by Shell et al. in their U.S. Pat. No. 4,304,765, incorporated herewith by reference. The matrix in solid form suitably is adapted for osmotic release, as described in U.S. Pat. No. 4,303,765, or it may be bioerodible, such that the active components are slowly released over a prolonged period of time, for example, from five to 15 days. A preferred polymeric matrix is a solid form comprising ethylcellulose, preferably constituting from about 79 to about 98 percent by weight of the composition. The solid form matrix or insert is manufactured, sized, shaped, structured and adapted for easy insertion and comfortable prolonged retention in the periodontal pocket. The matrix can have any geometric shape, and its dimensions can vary to conform to the subgingival site. The lower limit on the size of the matrix is governed by the amount of metronidazole to be housed and administered to elicit the desired pharmacological and periodontal response, as well as the smallest size of matrix that can be conveniently inserted and maintained in the pocket.

In another aspect, the invention concerns a method of periodontal treatment which comprises administering subgingivally a composition according to the invention in unit dose form within at least one periodontal pocket in one or more quadrants of the dentition. A preferred embodiment of the method is one where the metronidazole content of the composition is in a form adapted for sustained release.

SUMMARY

The Invention describes a novel method of treating advanced forms of periodontal disease that are associated with the proportional increase of anaerobic organisms such as spirochetes and black pigmented bacteroides. The invention involves the incorporation of metronidazole an antimicrobial which has a specific spectrum of activity against anaerobic bacteria, into an ethylcellulose film in such a way that the metronidazole is slowly released. The metronidazole ethylcellulose film is placed by the clinician directly into the periodontal pocket of 6 mm or more depth and left in situ for periods of 7 to 14 days or more during which time the metronidazole is continuously released at bacteriocidal levels for anaerobes. This manner of application assures that furcation sites on molars will be exposed to therapeutic levels of metronidazole. The release kinetics of the metronidazole can be controlled by the dimensions of the film and by the addition of polyethylene glycol. The activity of metronidazole can be enhanced by the usage of reducing agents.

DESCRIPTION OF THE PREFERRED EMBODIMENT

The invention and best mode of practicing the same is given hereafter by way of example and is presented for the purpose of illustration, but not of limitation.

EXAMPLE 1

Sustained Release Solid Form

| Component | Parts by Weight |
|---|---|
| Metronidazole | 1 to 20 |

Antioxidant, Ascorbic Acid 0.0 to 1.0
Ethyl Cellulose (Type N22, N7, or N-7NF)* 80 to 98
*Manufactured by Hercules, Inc., Delaware.

The ethylcellulose is dissolved in chloroform and then after complete dissolution, the metronidazole and antioxidant are added. The resulting mixture is cast on glass plates and after evaporation of the chloroform, the residual film is removed from the plate. Films of varying thickness and containing varying amounts e.g., from one to 20 percent, of metronidazole can be prepared. The films are to be cut to approximate the dimensions of the pocket (for example, 8 mm long by 3 mm wide by 0.5 mm thick) and then placed within the pocket by the dentist (See FIG. 3).

The latter film weighs about 12 mg. If metronidazole comprises 20 percent of this weight, then about 2.4 mg of metronidazole is added via the film to each infected pocket. If the patient has 20 such deep pockets, then about 50 mg (20×2.4 mg) of metronidazole is needed to treat the periodontal infection over a 7 to 14 day period. This dosage is about one one-hundredth (1/100th) the dosage of metronidazole currently given systemically to treat periodontal infections. This reduction in dosage is one of the important advantages of the the present invention over the systemic route of administration.

Other solid state polymers can be substituted in the composition to provide for equivalent or comparable sustained release of metronidazole in the pocket. Among these preferred are Vynathene, a soft and elastomeric vinyl acetate-ethylene copolymer and the biodegradable polymer, polycaprolactone, as described in U.S. Pat. No. 4,304,765 (J. Dent. Res. 60:Spec. Iss. IADR Abstracts, p.274).

In a modification of the invention, for faster sustained release, polyethylene glycol is dissolved in the chloroform with the other components, so as to give a final concentration of 10 percent. The 10 percent polyethylene glycol will result in a controlled faster release of the metronidazole from the polymer, which is especially useful in the prompt treatment of active periodontal infections. It should be obvious to anyone familiar with the art that metronidazole derivatives, such as those described in U.S. Pat. No. 3,700,685 other nitroimidazoles active against anaerobes, as well as other antimicrobial agents, such as chlorhexidine, fluoride, tetracyclines, penicillin and other compounds, could be incorporated singly or in various combinations in such a slow release device for the treatment of periodontitis.

The above formulations may optionally include excipient components, such self-sterilizing agents, flavoring agents, coloring or visualizing agents, and the like, in suitable proportion.

When compositions of this invention are placed in the periodontal pocket that exhibits bleeding and high proportions of spirochetes and black pigmented bacteroides in the subgingival plaque, highly favorable results are observed. For purposes of clinical proof of this result, human subjects of widely varied age groups, who have active periodontitis with pockets of 6 mm or more, can be used. Evidence of clinical effectiveness can be obtained in the following manner. Patients with 6 to 30 sites with pockets depths of 6 mm or more will be randomly assigned to one of two groups. Patients in group one will have ethylcellulose films containing metronidazole placed into these deep pockets, whereas patients in group two will have ethylcellulose films without metronidazole placed within their deep pockets. The film that is designated to be placed in the pocket will be contoured by the clinician so that it can be placed below the gingival margin, so as to occupy the majority of the space in the periodontal pocket (See FIG. 3). Prior to placement of these films in the pocket, the pocket depth and attachment distance will be measured as described previously, and an aliquot of plaque will be removed for microscopic and cultural analysis. The microscopic analysis will determine the numbers and proportions of various spirochetes, while the cultural analysis will determine the numbers and types of various black pigmented bacteroides species. The films will be left in place in the pockets for one or two-week periods. After this time the pocket depth, attachment distance and bacteriological measurements are repeated. Reduction in pocket depth, a decrease in attachment distance and a decrease in the proportions of spirochetes and black pigmented bacteroides species in the metronidazole-ethylcellulose-treated patients in comparison to the ethylcellulose-treated patients is an indication of the therapeutic effect of the metronidazole. Any free metronidazole in the periodontal pocket can be measured by a bioassay in which *B. gingivalis* is the test organism or by a high pressure liquid chromatographic procedure (See J. Pharm. Sci. 71:410, 1982). In a typical application of the invention an 8 mm length of the metronidazole-ethylcellulose film was inserted into a periodontal pocket of 6 mm depth. The 2 mm of film which extended out of the pocket was secured to the tooth by means of a cyanoacrylate glue so as to assure that the film would not be dislodged during chewing or by the subject's oral hygiene procedures. After 5 and 14 days in situ, 3 to 5 $\mu$g/ml of free metronidazole could be demonstrated in the fluid obtained from the pocket. After removal of the metronidazole ethylcellulose film from the pocket, it was shown to be capable in vitro of inhibiting the growth of *B. gingivalis*. These observations verify that the invention was acting as a slow release device for metronidazole in the periodontal pocket.

What is described to claim as my exclusive privilege or property in the invention, as described, is the following:

1. A film contoured to be cut to approximate the dimension of a periodontal pocket for the treatment of bacterial infections of the periodontum wherein the film consists essentially of a mixture of:
   80 to 98 parts by weight of ethylcellulose, 1 to 20 parts by weight of metronidazole, 0.1 to 1 part by weight of an antioxidant selected from the group consisting of ascorbic acid, sodium thiosulfate, dithiothreitol, cysteine, thioglycollate and glutathione.

2. A method of inhibiting the growth of a bacterial infection of the periodontum by placing locally into the periodontal pocket an antibacterial effective amount of the film of claim 1.

* * * * *